(12) United States Patent  
Dix et al.

(10) Patent No.: US 11,612,907 B2
(45) Date of Patent: Mar. 28, 2023

(54) FLUID DISPENSER

(71) Applicant: Vectair Systems Limited, Hampshire (GB)

(72) Inventors: Robert Dix, Hampshire (GB); Rebecca Anne Nelson, Bristol (GB); Jonathan Patrick Waller, Bristol (GB); Michael Philip Gray, Bristol (GB); Frederick Charles Ridout, Bristol (GB)

(73) Assignee: Vectair Systems Limited, Basingstoke (GB)

( * ) Notice: Subject to any disclaimer, the term of this patent is extended or adjusted under 35 U.S.C. 154(b) by 192 days.

(21) Appl. No.: 16/656,020

(22) Filed: Oct. 17, 2019

(65) Prior Publication Data

US 2020/0122181 A1   Apr. 23, 2020

(30) Foreign Application Priority Data

Oct. 17, 2018  (GB) ..................... 1816922

(51) Int. Cl.
  *B05B 17/06*   (2006.01)
  *B05B 17/00*   (2006.01)
  *B05B 9/04*    (2006.01)

(52) U.S. Cl.
  CPC ........ *B05B 17/0646* (2013.01); *B05B 9/0413* (2013.01); *B05B 17/0653* (2013.01)

(58) Field of Classification Search
  CPC .............. B05B 17/0646; B05B 9/0413; B05B 17/0653; B05B 17/0676; A61L 2209/11; A61L 2209/132; A61L 2209/133; A61L 9/14
  See application file for complete search history.

(56) References Cited

U.S. PATENT DOCUMENTS 7,770,757 B2 *  8/2010  Helmlinger ....... A61M 15/0065
                                                     222/189.11
9,333,523 B2 *  5/2016  Lowy ..................... B05B 15/58
2004/0139963 A1  7/2004  Ivri et al.
(Continued)

FOREIGN PATENT DOCUMENTS

JP         2010-023875 A      2/2010
WO    WO 2014/071710 A1      5/2014
(Continued)

OTHER PUBLICATIONS

UK Intellectual Property Office, Search Report, Application No. GB1816922.7, dated Mar. 5, 2019, 3 pages.
(Continued)

*Primary Examiner* — Qingzhang Zhou
(74) *Attorney, Agent, or Firm* — Sunstein LLP

(57) ABSTRACT

A dispenser capable of dispensing a fluid via a vertically-oriented piezo device comprises a reservoir in the form of a replaceable cartridge containing a fluid to be dispensed, a planar piezo element having front and rear surfaces and which in use is oriented with its plane vertical and which is drivable to vibrate and thereby dispense fluid from the front surface, and a pump to draw a predetermined amount, or dose, of fluid from the reservoir and to drive the dose of fluid at a predetermined above-atmospheric pressure to the rear surface of the piezo element for dispensing.

11 Claims, 2 Drawing Sheets

(56) References Cited

U.S. PATENT DOCUMENTS

Figure 1:
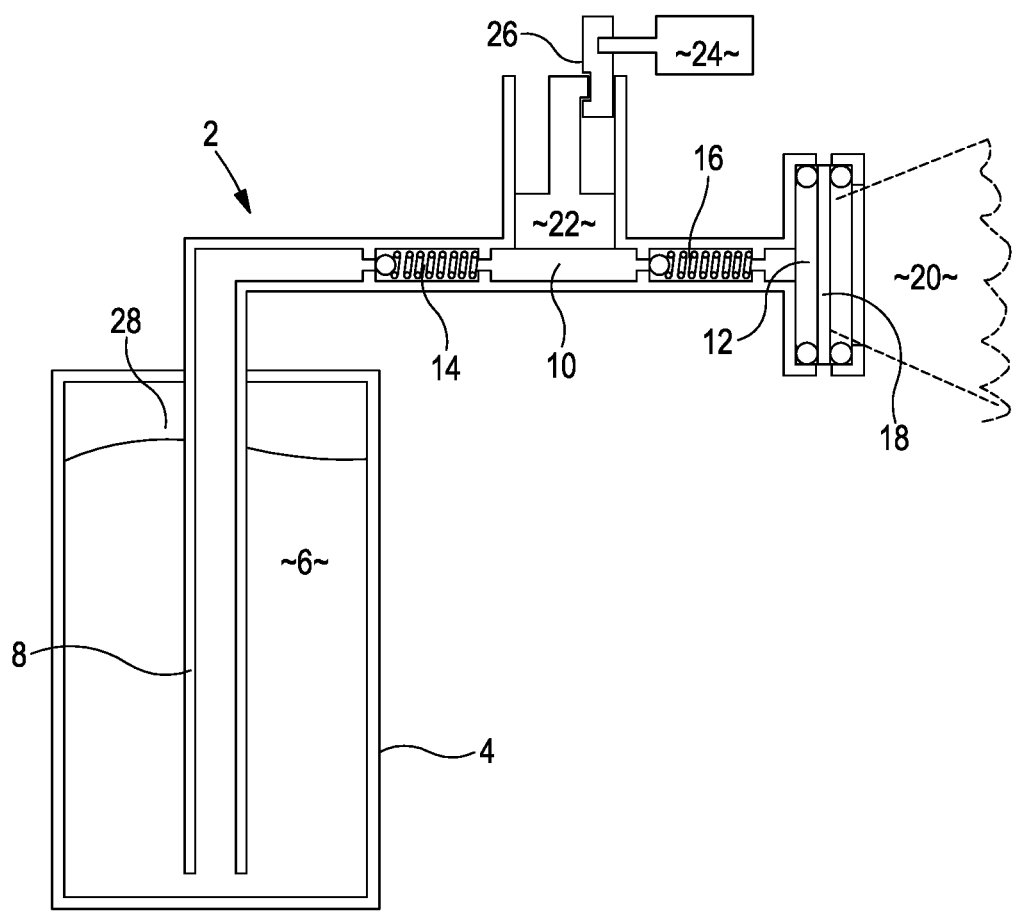
Figure 2:
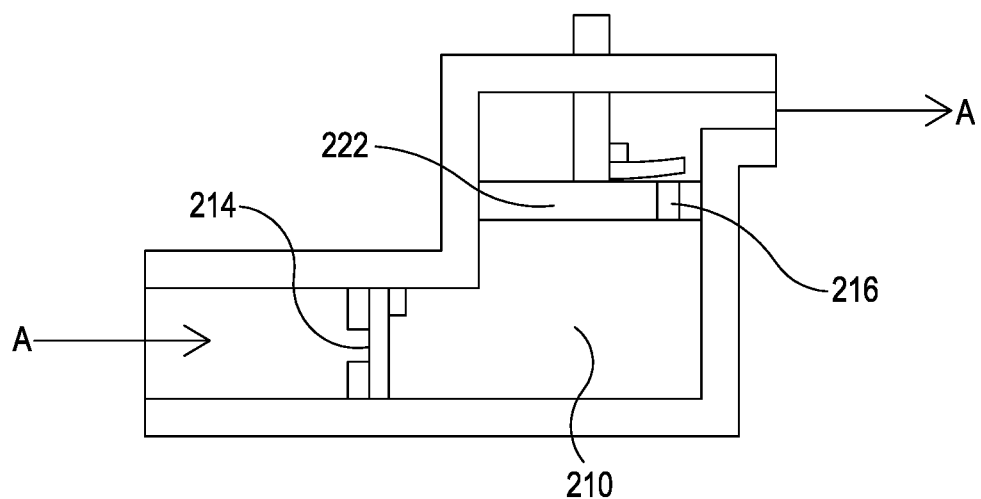

2006/0243740 A1* 11/2006 Reynolds ............ A47K 5/1208
                                                          222/52
2006/0289679 A1    12/2006 Johnson et al.
2008/0290185 A1    11/2008 Duru
2012/0285564 A1*  11/2012 Airaksinen ........... G01F 11/021
                                                        137/565.01
2013/0327322 A1*  12/2013 Bentvelsen ......... B05B 17/0676
                                                        128/200.16

FOREIGN PATENT DOCUMENTS

WO    WO 2015/033214 A2    3/2015
WO    WO2015033214      *  3/2015  ............. B05B 15/58
WO    WO 2018/172561 A1    9/2018

OTHER PUBLICATIONS

European Patent Office, Extended European Search Report, Application No. 19203790.1, dated Dec. 12, 2019, 8 pages.

* cited by examiner

FLUID DISPENSER

CROSS-REFERENCE TO RELATED APPLICATIONS

This application claims priority from United Kingdom Patent Application Serial No. GB1816922.7, filed on Oct. 17, 2018, which is hereby incorporated by reference, in its entirety.

FIELD OF THE INVENTION

The present invention relates to a dispenser which can be used to dispense any of a variety of materials, mainly liquids, into an aerosol form, such as (but not limited to) air freshening compositions or other chemicals requiring automatic dosing.

BACKGROUND ART

Dispensers are commonly provided in washrooms and similar facilities, in order to improve their overall environmental condition. In the past, various solid materials were utilized which sublimated, thereby dispersing a substitute odour for the odour found in public facilities. In order to enhance the dispersion of such sublimating materials, many suppliers developed powered fan devices which assisted in the dispersal of the sublimated material. Such devices are well known in the art, and an example is shown in U.S. Pat. No. 4,830,791, which discloses a solid dispensing device.

More recently, odour control devices where a pressurized aerosol container is utilized have become well known in the art. Aerosol-type dispensing devices typically include a battery-powered motor that actuates the nozzle on the aerosol container on a periodic basis. These conventional dispensing devices have significant disadvantages. Aerosol cans require propellant gases, and whilst CFC-free propellants have been identified, these tend to require volatile organic compounds (VOCs), propanol, isobutanes and the like which are coming under increasing scrutiny. Several jurisdictions have introduced legislation aimed at reducing or elimination the unnecessary use of such chemicals.

It would therefore be desirable to deliver the scent directly, i.e. by evaporation or other dispersion of the scent composition itself, avoiding the need for carrier and propellant chemicals. This has been achieved for the home environment by SC Johnson, Inc. with the Glade® Wisp device, which uses a piezo element to disperse a scent formulation into the air by vibrating at high frequency while in contact with a small volume of the formulation. This aerosolises the formulation, dispersing it as required. However, such devices are problematic in that the volume of formulation that is in contact with the piezo must be closely controlled; if too large, the piezo does not resonate and the formulation is not dispensed. This requires the formulation to be delivered to a horizontally-disposed piezo element via a wick. This is acceptable for home use, where the device will be mounted at a low location within the room. Thus, the fragrance is dispensed upwards into the room. However, it is unsuitable for use in corporate or communal washrooms, where the dispenser must be fitted high up to limit vandalism or other tampering. The use of a Wisp-type device in such a location would not result in an effective dispensing of the fragrance into the room, as most of the fragrance would be captured by the ceiling panel above the device.

We created a device which controls the rate of flow of a fragrance formulation onto a vertically-oriented piezo device, as described in EP2564878 and U.S. Pat. No. 9,636,431; this provides an effective fragrance dispenser that can be mounted in an elevated location (typically more than 6 feet or 2 metres from the floor) and that can dispense a fragrance at regular intervals without the use of excessive propellant compositions and the like. This dispenser is a battery-operated piezo-based dispenser suitable for use in corporate and communal environments (it is preferable for the device to be battery-operated, rather than a plug-in device requiring a mains electrical supply, as there is rarely a mains electrical supply at the required location), which avoids all propellant gases and reducing the VOC usage dramatically. This dispenser includes a reservoir located in use generally above the porous piezo element, so that the effective fluid column extending above the element exerts pressure to the rear of the piezo element. The earlier invention was directed to reducing this pressure, in line with the common understanding that the pressure on the rear of the piezo element should be limited, particularly during dispensing, because such piezo elements are sensitive to the pressure of fluid behind them; if the pressure is too high the piezo element will be too heavily damped to be able to vibrate in the correct manner. The earlier design provided means to reduce the fluid pressure behind the piezo element and ensured that an acceptably low pressure was maintained in combination with a useful flow rate; however, we now wish to improve the accuracy with which fluid is dispensed. This need for accuracy relates to the amount of fluid which is dispensed (or "dose") each time the dispenser is actuated and also the characteristics of the plume of dispensed material are optimised (the plume angle and its length are important for ensuring the dispensed fluid is dispensed as intended into the space in which the dispenser is located). Dispensers are commonly fitted with a refillable and/or replaceable container, or reservoir, containing the fluid to be dispensed; it is also important that the accuracy with which fluid is dispensed can be reliably maintained over time, so that the refill/replacement of the reservoir (which is usually carried out according to a predetermined timetable) does not take place too soon, before the reservoir is empty (which would lead to a waste of fluid), and also that it does not take place too late, after the reservoir has been empty for some time (which would mean that the dispenser had not been capable of performing its function for some time). We have also found that ambient factors, such as temperature, humidity, air pressure and the like, can have a significant effect on the amount of fluid which is dispensed and, where these ambient factors are changeable, this too affects the amount of fluid which is dispensed. In addition, although the fluid behind the porous piezo element tends to be retained by the effects of surface tension, over prolonged periods there can be fluid leakage, which not only wastes fluid but also adversely affects the predictability of the reservoir refill/replace interval.

SUMMARY OF THE INVENTION

The present invention is predicated on the realisation that an improved dispenser can be designed if the generally accepted preconception that piezo dispensers should not have any significant fluid pressure behind them during the dispensing operation is not followed. Accordingly the present invention provides a dispensing apparatus comprising a reservoir containing a fluid to be dispensed, a planar piezo element having front and rear surfaces and which in use is oriented with its plane vertical and which is drivable to vibrate and thereby dispense fluid from the front surface, and a pump to draw a predetermined amount, or dose, of fluid from the reservoir and to drive the predetermined amount of fluid at a predetermined above-atmospheric pressure to the rear surface of the piezo element for dispensing.

Figure 3:
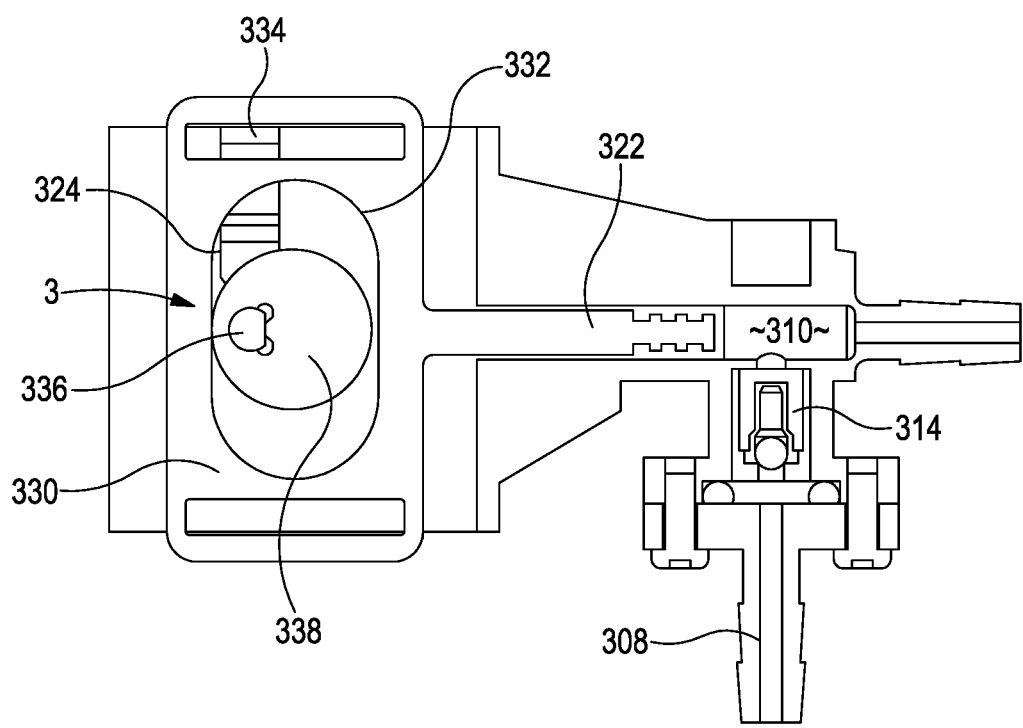

When it is desired to dispense fluid, such an arrangement allows an accurately measured dose of fluid to be drawn into an intermediate chamber and then to dispense the fluid through the piezo element so that it is atomised and dispersed in a precisely controlled manner. This enables reliably accurate dispensing of the fluid over time, allowing the life of the reservoir to be predicted with greater accuracy than with conventional dispensers. The piezo element may be porous, thereby to permit dispensing from the front surface of the element of fluid contacting the rear surface of the element. Preferably the dispenser is arranged so that there is no fluid pressure acting on the rear surface of the piezo element at times when the dispenser is not dispensing fluid, which reduces leakage of fluid. The predetermined above-atmospheric pressure is set according to the shape, dimensions, hole size or porosity of the piezo element and the rate at which it is caused to vibrate, so that the fluid is driven with a substantially constant pressure which is a matter of design so that it works in concert with the vibrations of the piezo element to produce an optimised plume of atomised fluid. We intend that the term "vertical" used herein be interpreted broadly, so as to accommodate a tolerance of 5°, 10° or up to 15° away from the vertical.

The pump can be a reciprocating piston pump, the drawing of the fluid from the reservoir and the driving of the fluid for dispensing defining a single cycle of the pump, so that the pump cycle can consist of two separate strokes of the reciprocating piston—for simplicity and economy these two strokes can be successive movements of the reciprocating piston in opposite directions, a filling stroke in one direction of piston movement and a dispensing stroke in the next subsequent movement of the piston in the opposite direction. The dispenser may include two one-way valves, so that the apparatus can include a pumping chamber, one one-way valve adapted to allow fluid to flow into the pumping chamber from the reservoir and the other one-way valve adapted to allow fluid to flow out of the pumping chamber into a dispensing chamber at the rear surface of the piezo element, the reciprocating piston being effective to vary the volume of the pumping chamber, thereby selectively to draw fluid from the reservoir into the pumping chamber or to drive fluid from the pumping chamber into the dispensing chamber. In this way the drawing of a precise amount of fluid into the pumping chamber and the accurate driving of the fluid dose at the predetermined above-atmospheric pressure for dispensing can be achieved by accurate control of the movement of the piston pump.

The one-way valve allowing fluid to flow out of the pumping chamber into the dispensing chamber may be located closely adjacent to the rear surface of the piezo element, so as to allow the volume of the dispensing chamber to be minimised relative to the volume of the pumping chamber. This means that, at the end of each dispensing operation only a very small amount of fluid remains behind the piezo element and this is retained in place by surface tension and/or gravity and thus reduces wasteful leakage of fluid when the dispenser is not operating.

The reciprocating piston pump could be driven by a rotary motor which is connected to the reciprocating piston by a linkage, the motor and the linkage being adapted to cause the piston to move through a dispensing stroke at a set rate so that the fluid in the pumping chamber is made to flow to the dispensing chamber at a substantially constant flow rate throughout the dispensing stroke as the pump drives the predetermined amount of fluid at above-atmospheric pressure to the rear surface of the piezo element. The motor and the linkage are preferably adapted to cause the piston to move through a filling stroke at a predetermined rate, so that the predetermined amount of fluid is drawn from the reservoir into the dispensing chamber. A relatively simple and inexpensive linkage can be in the form of a cam and/or a scotch yoke.

In use the piezo element is preferably positioned vertically above the level of the top surface of the fluid in the reservoir. This ensures that during operation of the dispenser during the dispensing stroke the only pressure acting on the rear surface of the piezo element is the predetermined above-atmospheric pressure caused by the pump, and that other than during operation of the dispenser during the filling stroke and after the dispensing stroke there is no fluid pressure acting on the rear surface of the piezo element; this adds to dispensing accuracy and reduces leakage.

There may be a controller arranged to actuate the pump in concert with the piezo element, and the controller can be arranged to as to actuate the piezo element before actuating the pump, and/or to cause the piezo element to vibrate throughout the time the pump is driving the predetermined amount of fluid at above-atmospheric pressure to the rear surface of the piezo element and for a period after the pump has stopped driving fluid to the rear surface of the piezo element. The reservoir can be a replaceable/refillable cartridge which is removably mounted in the apparatus.

BRIEF DESCRIPTION OF THE DRAWINGS

The invention will now be described by way of example and with reference to the accompanying figures, in which;

FIG. 1 is a schematic side view in cross-section showing how a dispenser in accordance with the invention would operate;

FIG. 2 is a schematic illustration of an alternative pump arrangement for use with the dispenser of FIG. 1, and FIG. 3 is a schematic side view of a linkage arrangement for use with the dispenser of FIG. 1.

DETAILED DESCRIPTION OF THE EMBODIMENTS

FIG. 1 shows a dispensing apparatus 2 comprising a reservoir 4 containing a liquid 6 which is to be dispensed. A dip tube 8 for drawing the liquid out of the reservoir 4 extends downwardly into the reservoir 4, reaching almost to its bottom so as to ensure that nearly all of the fluid 6 can be dispensed before the reservoir 4 has to be refilled or exchanged for a full replacement.

The dip tube 8 is in fluid communication with a pumping chamber 10, which in turn is in fluid communication with a dispensing chamber 12. Between the dip tube 8 and the pumping chamber 10 is a first one-way valve 14, and between the pumping chamber 10 and the dispensing chamber 12 is a second one-way valve 16; one-way valves 14, 16 are spring-loaded ball valves as ball arranged to work in opposition for reasons described below. The dispensing chamber is closed by a commercially-available planar piezo plate 18, which is porous and in use vibrates so as to atomise the fluid and disperse it in a plume 20. The pumping chamber 10 is closed by a reciprocating piston 22 which can reciprocate in a vertical direction (in use and as shown in the drawing), driven by a rotary motor 24 acting through linkage 26 (described in more detail below with reference to FIG. 3). It will be noted that the piezo element 18 is positioned above the highest level of the top surface 28 of the fluid 6 in the reservoir 4.

In operation, the piston 22 is drawn upwardly by motor 24 acting through linkage 26; this causes a drop in pressure in pumping chamber 10, which causes the balls to move to the right, and one-way valve 14 to open and one-way valve 16 to close. Continued movement of piston 22 in the same direction draws fluid 6 from the reservoir 4 through the dip tube 8 and fills the pumping chamber. When piston 22 reaches its highest level and reverses direction downwardly, this causes the fluid pressure within pumping chamber 10 to increase, which moves the balls to the left, and closes one-way valve 14 and opens one-way valve 16. Further downward movement of the piston 22 drives the fluid from the pumping chamber 10 into the dispensing chamber 12; here the fluid pressure, in combination with the vibration of the piezo plate 18 causes the fluid to pass through the plate and be atomised and dispersed in a plume 20. Dispensing of the fluid in plume 20 continues until piston 22 reaches the limit of its downward motion, at which point the pumping cycle is completed and the dispenser 2 is ready to begin another dispensing operation, without delay if desired. It should be noted that the relative sizes of the pumping chamber 10 and the dispensing chamber 12 as shown in the drawings is purely schematic, in practice the volume of the dispensing chamber 12 is much smaller than that of the pumping chamber, and dispensing chamber 12 is shaped and the one-way valve 16 located relative to piezo element 18 so as to allow the volume of dispensing chamber 12 to be made a small as possible. This ensures that when the dispensing stroke is completed and one-way valve 16 closes, the amount of liquid remaining in dispensing chamber 12 is small enough to be atomised and dispensed by the vibrating action of the piezo element 18 alone, meaning that there is little fluid left which can leak from dispensing chamber 12 when the dispenser 2 is in standby mode, between dispensing operations.

The pump and valve arrangement can be any which utilises the strokes of a reciprocating piston; an alternative arrangement is shown in FIG. 2, in which one one-way valve 214 is located as in FIG. 1, but the second one-way valve 216 is located in the piston 222. This arrangement operates so that fluid flows into and out of the pumping chamber 210 in the general direction indicated by the arrows A. Downwards motion of piston 222 closes one-way valve 214 and opens one way valve 216; fluid in the pumping chamber 210 below the piston 222 flows through the one-way valve 216 so that it is above the piston 222. When the piston changes direction, one-way valve 214 opens and one-way valve 216 closes; continued upwards movement of the piston 222 causes fluid to be drawn into the pumping chamber 210 beneath the piston 222, whilst the fluid already in the pumping chamber 210 above the piston is driven away to be dispensed. When the piston reaches the end of its upwards motion the pumping cycle is complete, and ready to be repeated.

FIG. 3 shows a linkage mechanism 3 suitable for controlling the movement of the reciprocating piston 322 on both directional strokes, to ensure a sufficiently constant fluid pressure and flow rate on the dispensing stroke so that a metered dose of fluid is passed to the piezo element to be efficiently atomised and dispersed, and to draw in an accurately metered dose of fluid into the pumping chamber 310 on the pumping stroke. The mechanism 3 illustrated is intended to operate in the same way as that shown in FIG. 1, but here only one one-way valve 314 and a shortened dip tube are shown, and there is no dispensing chamber or piezo element shown. The end of the piston 322 distant from the dispensing chamber 310 is enlarged in a flat yoke 330; this yoke is provided with a yoke slot 332 and two guide slots 344 which engage with tabs (not shown) to ensure that both ends of the piston 322 can only reciprocate along one axis (which is parallel to the slots 334). Rotary motor 324 drives a spindle 336 about an axis perpendicular to the plane of the drawing, and san off-centre circular cam 338 is fixed to the end of the spindle 336 so as to engage with the inside of yoke slot 332, forming a modified scotch yoke. The amount of offset between the centre of the spindle 336 and the centre of the circular cam 338, the radius of the circular cam 338 and the rate of rotation are all significant in ensuring that the movement of the piston 322 is controlled as required (as described above). The surface area of the end of the piston in the dispensing chamber and the length of the piston stroke are relevant to the volume of each dose of fluid dispensed in one pumping cycle.

In our presently preferred embodiment, each metered dose is about 0.05 ml, and is drawn from a replaceable cartridge containing 100 ml when full with a dose accuracy of 6%. A controller such as a suitably programmed microprocessor is included in the dispenser (along with a suitable power source, such as a battery) to actuate the dispenser at regular intervals, which may be varied by the user, usually at any frequency between every 14 minutes and every hour. The controller may switch off the dispenser completely for a prolonged and user-selectable period (overnight, for example) and turn it on for one or more different user-selectable periods at certain times (for the hours around mealtimes, for example). The controller can also be set to control the piezo element so as to have a duty cycle of anything between about 1 second and about 6 seconds and the motor so as to have a duty cycle of between about 10 seconds and about 25 seconds, and at each dispense stroke the controller causes the piezo element to vibrate at about 123 kHz, starting just before the dispensing stroke begins and continuing for a short period after the dispensing stroke has ended. A particular configuration we have used delivers a dose for a piezo element cycle of about 3.5 seconds every 20 minutes or so for 2222 cycles (about 30 days) at which point the dispenser stops for the cartridge containing the fluid to be replaced/refilled.

It will of course be understood that many variations may be made to the above-described embodiment without departing from the scope of the present invention. For example, the circular cam could be replaced with a non-circular cam, with the shape of the cam being chosen to give a specific profile to the movement of the piston over time. There may be a button or switch on the dispenser to actuate a single dispensing cycle. There may be a light or some other indicator to show when dispensing is in progress, and/or about to start. The reservoir could be a stiff cartridge, a flexible pouch, or it could be a flexible pouch within a rigid outer cartridge. The controller could be provided with means such as a radio receiver so as to be remotely manually operable or so that any setting could be varied remotely, and it could have a transmitter so it could signal if it is not operating properly or if it is empty and the cartridge needs changing. Although described with fragrance dispensers in mind, the invention could be used in any application where frequent doses of atomised fluid need to be dispersed, such as in greenhouses or in agricultural applications where the fluid could be a selective poison (e.g. weed or pest killer) or a beneficial growth agent (e.g. a fertilising compound), or in particular atmospheric conditions (such as a fungicide in a particularly humid atmosphere). The dispenser may be programmed to prime itself before a dispense stroke, should the particular fluid, dispenser or ambient conditions make this necessary.

Where different variations or alternative arrangements are described above, it should be understood that embodiments of the invention may incorporate such variations and/or alternatives in any suitable combination.

What is claimed is:

1. A dispensing apparatus comprising a reservoir containing a fluid fragrance formulation to be dispensed, a planar piezo element having front and rear surfaces and which in use is oriented with its plane vertical and which is drivable to vibrate and thereby dispense fluid fragrance formulation from the front surface, a reciprocating piston pump having a reciprocating piston to draw a predetermined amount of fluid fragrance formulation from the reservoir into an intermediate pumping chamber and to drive the predetermined amount of fluid fragrance formulation at a predetermined above-atmospheric pressure from the intermediate pumping chamber to a dispensing chamber at the rear surface of the piezo element for dispensing, a first one-way valve which allows fluid fragrance formulation to flow out of the intermediate pumping chamber into the dispensing chamber at the rear surface of the piezo element, and a second one-way valve which allows fluid fragrance formulation to flow into the intermediate pumping chamber from the reservoir, the reciprocating piston being effective to vary the volume of the intermediate pumping chamber, thereby selectively to draw fluid fragrance formulation from the reservoir into the intermediate pumping chamber or to drive fluid fragrance formulation from the intermediate pumping chamber into the dispensing chamber, the first one way valve being located adjacent to the rear surface of the piezo element so as to minimise the volume of the dispensing chamber relative to the volume of the intermediate pumping chamber.

2. A dispensing apparatus according to claim 1 in which the piezo element is porous, thereby to permit dispensing from the front surface of the element of fluid fragrance formulation contacting the rear surface of the element.

3. A dispensing apparatus according to claim 2 in which the drawing of the fluid fragrance formulation from the reservoir and the driving of the fluid fragrance formulation for dispensing is a single cycle of the pump, the pump cycle consisting of two separate strokes of the reciprocating piston.

4. A dispensing apparatus according to claim 1, in which the reciprocating piston pump is driven by a rotary motor which is connected to the reciprocating piston by a linkage, the motor and the linkage being adapted to cause the piston to move through a dispensing stroke at a set rate so that the fluid fragrance formulation in the pumping chamber is made to flow to the dispensing chamber at a substantially constant flow rate throughout the dispensing stroke as the pump drives the predetermined amount of fluid fragrance formulation at above-atmospheric pressure to the rear surface of the piezo element.

5. A dispensing apparatus according to claim 4, in which the motor and the linkage are adapted to cause the piston to move through a filling stroke at a predetermined rate so that the predetermined amount of fluid fragrance formulation is drawn from the reservoir into the dispensing chamber.

6. A dispensing apparatus according to claim 4 in which the linkage comprises a cam and/or a scotch yoke.

7. A dispensing apparatus according to claim 1, in which the piezo element is in use positioned vertically above the level of the top surface of the fluid fragrance formulation in the reservoir.

8. A dispensing apparatus according to claim 1, further comprising a controller to actuate the pump in concert with the piezo element so as to dispense fluid fragrance formulation.

9. A dispensing apparatus according to claim 7, in which the controller is adapted to actuate the piezo element before actuating the pump.

10. A dispensing apparatus according to claim 7, in which the controller is adapted to cause the piezo element to vibrate throughout the time the pump is driving the predetermined amount of fluid fragrance formulation at above-atmospheric pressure to the rear surface of the piezo element and for a period after the pump has stopped driving fluid fragrance formulation to the rear surface of the piezo element.

11. A dispensing apparatus according to claim 1 in which the reservoir is removably mounted in the apparatus.

* * * * *